United States Patent [19]
Forehand

[11] Patent Number: 5,416,335
[45] Date of Patent: May 16, 1995

[54] AUTOMATED VISUAL INSPECTION SYSTEM FOR DETERMINING THE SET POSITIONS OF A ROW OF DIP SWITCHES

[75] Inventor: Monty A. Forehand, Yukon, Okla.

[73] Assignee: Seagate Technology, Inc., Scotts Valley, Calif.

[21] Appl. No.: 228,596

[22] Filed: Apr. 15, 1994

[51] Int. Cl.⁶ .................. G01N 21/86; G01V 9/04
[52] U.S. Cl. ........................... 250/561; 250/229
[58] Field of Search .......... 250/229, 561, 221; 348/94, 95, 86, 87

[56] References Cited

U.S. PATENT DOCUMENTS

| | | | |
|---|---|---|---|
| 4,429,219 | 1/1984 | Yochum et al. | 250/229 |
| 4,634,861 | 1/1987 | Ching et al. | 250/231 SE |
| 4,731,530 | 3/1988 | Mikan | 250/229 |
| 4,919,512 | 4/1990 | Flaherty | 350/96.29 |
| 5,177,355 | 1/1993 | Branan, Jr. | 250/229 |

Primary Examiner—David C. Nelms
Assistant Examiner—Steven L. Nichols
Attorney, Agent, or Firm—Westman, Champlin & Kelly

[57] ABSTRACT

A method and apparatus for visually inspecting a discrete DIP switch block on a circuit card and analysis of the physical position of each switch. A comparison of reflected light intensities from each of the horizontally oriented switch faces is performed to determine the relative position of the switches. An output is provided based upon the comparison.

14 Claims, 3 Drawing Sheets

5,416,335

AUTOMATED VISUAL INSPECTION SYSTEM FOR DETERMINING THE SET POSITIONS OF A ROW OF DIP SWITCHES

BACKGROUND OF THE INVENTION

This invention relates to automated visual inspection of relative position components. More specifically, the invention relates to machine vision inspection of dual inline package (DIP) switches.

The background of machine vision systems is known. Many systems of optical sensors and comparators of the optical sensor's output are used in industry to inspect or monitor processes or systems of manufacturing. The basic elements of a machine vision system are elements of image acquisition, image processing, data analysis and interface to a user or a host system. Each of these elements is implemented by several technologies or techniques. In a general sense, current machine vision systems have difficulty overcoming the inherent environmental asymmetries in any real process or system. More specifically, it is difficult to resolve process parameters under variable light conditions and variable inspection piece orientations.

There are many types of equipment for each element of a machine vision system. An analog camera or ridicon is a basic technology commonly used in image acquisition. By digitizing a video signal, a digital image is formed. Many of the machine vision systems use solid state cameras. In many instances, the solid state camera is a charged coupled device (CCD) camera that acquires a digital video image of a component to be inspected. Pixel resolution is also a measure of the cameras sensitivity as well as the resolution of the digital processing unit in the image processor. The more sensitive a camera is, the more detail can be captured in the image. This sensitivity can also be a weakness as it can receive erroneous data should a variation in lighting occur.

Another device is a line scan camera (LSC) which only scans in a single line of an image at a time. The LSC uses the motion of a component on an position translation device to move the component beneath the camera to generate the digitized image line by line. The fact that the line scan camera only records a single line of the digital image at any single point in time makes the digital image even more susceptible to light variations and motion perturbations. The intolerance of the line scanning device to variations in a process flow are significant concerns and costs to a process designer that uses a vision system for automated component comparation.

There are a substantial number of methods utilized in designing a vision system for processing of the digitized image. Many image acquisition systems have the ability to provide either a binary black and white image, a grey scale image, or a color image to the image processing system. Each type of image offers advantages and disadvantages to the process designer in designing a visual inspection system. A grey scale image is typically made up of 256 or more levels of resolution per pixel recorded. A standard notation of gray scale levels represents each level in a range from 0 (black) to 255 (white). Color systems are also known.

Image analysis can require that a captured image be identified or related back to a desired or known image. This analysis can include reorientation of the image to be accurately compared to a known quantity. Either the image must be rotated in actual process flow to guarantee that the image is captured in correct orientation; or in post image capture, the part must be rotated via software and compared to a known master image.

SUMMARY OF THE INVENTION

An apparatus and method for visually inspecting a discrete DIP switch block and analysis of the physical positions of each switch on the block is provided. The apparatus includes an image recording device, image processor, memory storage and a display and monitoring device, that resolves a digitized image into a binary representation of the switches and their respective light intensities reflected from a light source. The intensities are determined for each switch face, and the differential in light intensities on the switch faces resolves the switch physical position. A comparison of desired positions in a look-up table or by other means passes or rejects the scanned switch block. The user interface notifies either a human or machine user for further disposition of the parts. The method performs a comparison of reflected light intensities from each of the horizontally oriented switch faces and determines the relative position of the switches. The resolved apparent position of the switches is compared against a desired position. Incorrect switch position warnings are conveyed to a monitoring interface.

DETAILED DESCRIPTION OF THE PREFERRED EMBODIMENTS

The present invention is directed towards the accurate sensing and resolution of Dual Inline Package (DIP) switch positions emplaced on printed circuit boards. One skilled in the art of visual image processing systems will recognize that inspection of any discrete variable position element can be implemented utilizing the technique and apparatus set forth herein.

Figure 1:
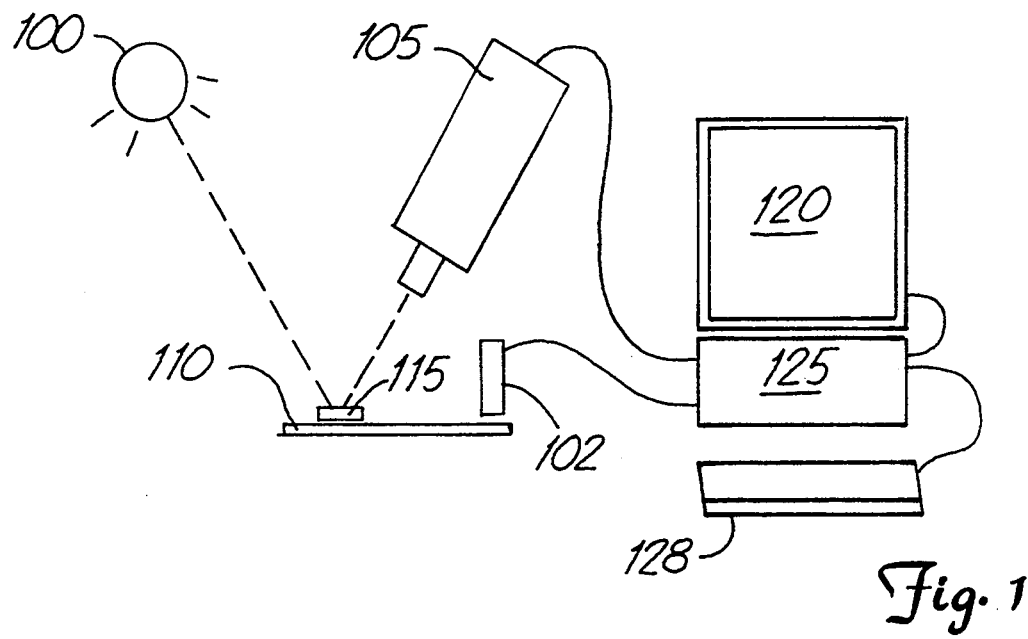
FIG. 1 is a system diagram of the image analysis of the present invention.
Figure 2:
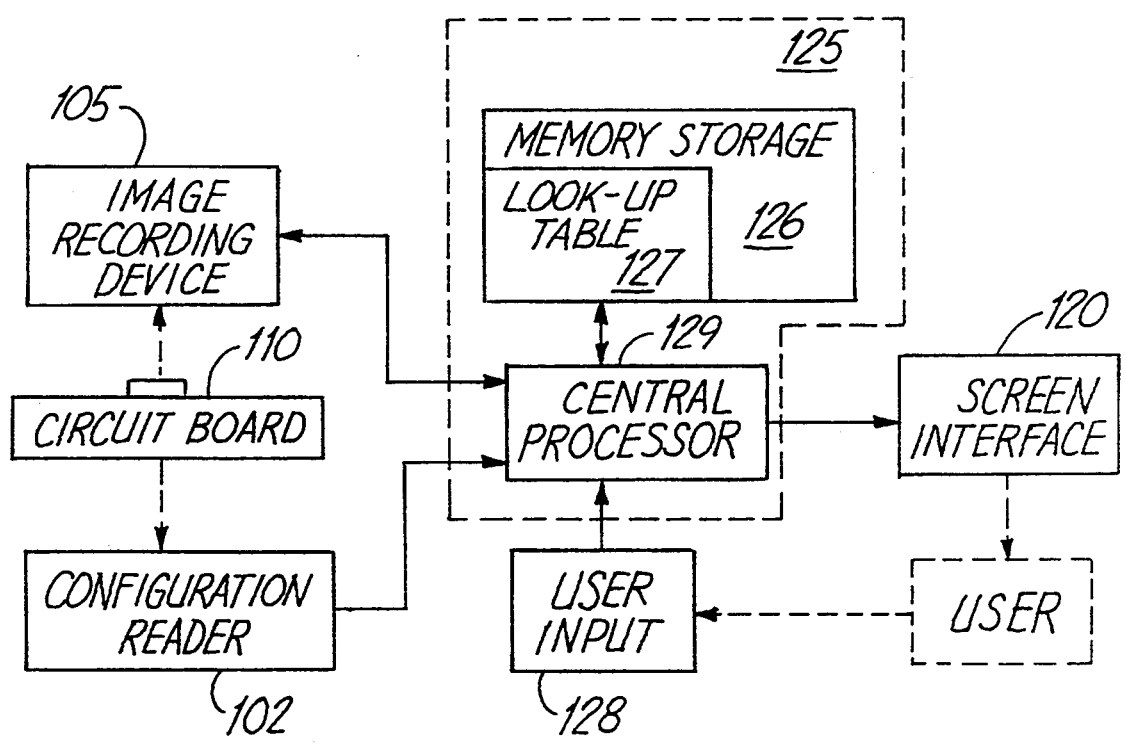
FIG. 2 is a block diagram of FIG. 1.
Figure 4:
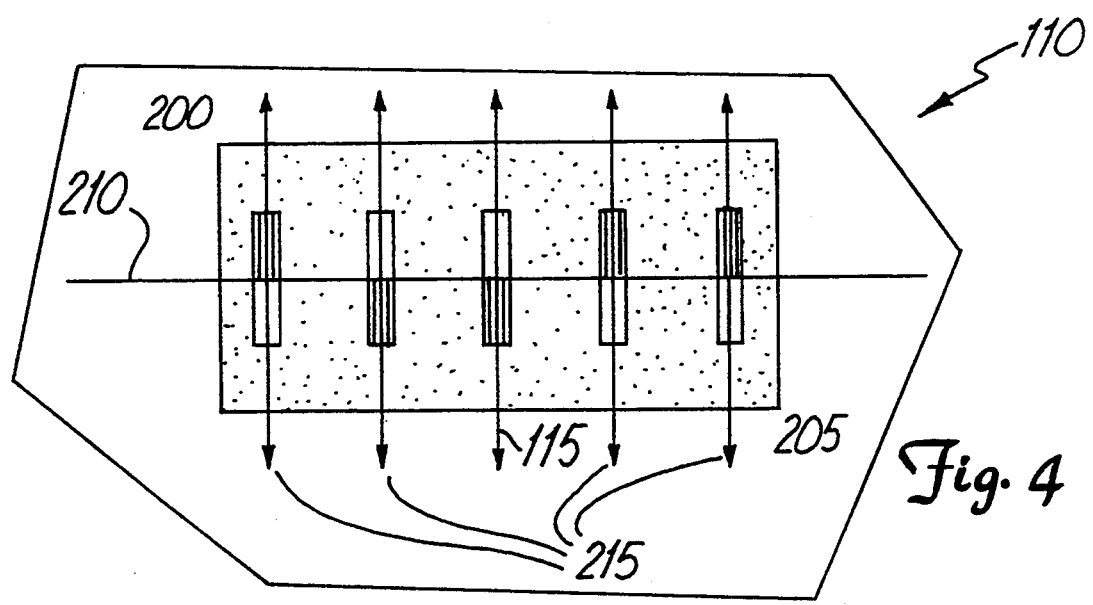
FIG. 4 is an image of a DIP switch block with position centerlines defined.

FIG. 1 shows circuit board 110 positioned under camera 105 which records the digital image of circuit board 110 with DIP switch housing 115. Camera 105 couples to image processor 125 having monitor 120 and keyboard input 128. The desired configuration of DIP switch housing 115 is either read from the surface of the circuit card via optical sensor 102 (i.e. bar code reader) or looked up on table 127 resident in image processor memory 126 (FIG. 2). Camera 105 may be angled between 15° and 45° from vertical and viewing can be done with standard office or factory fluorescent lighting 100. Camera 105 captures an image of circuit board 110 which is captured in digital format or converted into a digital image. The image is processed by passing the digitized image through a threshold filter or the image is filtered in software to reduce the grey scale image to a binary image that highlights DIP switch housing 115 as a block of black pixels surrounded by white pixels. Each switch's position is resolved as varied intensity pixels tending toward white in the higher reflecting switch face and varied intensity pixels tending toward black on lower reflectance switch face. The binary image is analyzed to locate DIP switch housing 115 location. The image analyzer recognizes edges of DIP switch housing 115 and locates a horizontal centerline 210 of switch 215 (FIG. 4 By following horizontal centerline 210 of DIP switch housing 115, locations of each of individual DIP switches are resolved. Vertical centerlines 215 of each switch are calculated and the centerline row of pixels is sampled for each switch face and the intensity of the pixels is averaged over the number of pixels sampled. The relative position of the individual switches is resolved by the processing of the relative intensity differential of the each half of the individual switch. The position of the DIP switches is compared against the desired position of the switches in a comparator file defined either by the board configuration or by operator input. If a nonconforming switch is sensed, board 110 may then be diverted for rework, or the operator is notified by a sensory alert signal to correct the switch position.

The image acquisition system in a preferred embodiment is grey scale solid state camera 105 that records the image with sufficient detail to resolve an apparent reflected light differential in the DIP switch position on circuit board 110. Digitizing camera 105 preferably has a minimum resolution of 512×512 discrete pixels per image. Camera 105 is mounted at an angle over board 110 to use background light reflecting off the work piece. In one embodiment, a light intensity of 3 W/ft$^2$ (e.g. standard industry fluorescent lighting environment) 100 is used to achieve good inspection results. This reflected light processing is well suited for a typical industrial assembly area that has consistently positioned light sources but not necessarily consistent light intensity. Camera 105 field of view should be adjusted to frame DIP housing 115 area plus an effective surrounding area to account for placement or orientation errors in the placement of circuit card 110. In one embodiment, camera 105 focus is fixed with a field of view sufficient to effectively process circuit card orientation variations up to 30 degrees offset from normal. Camera 105 is typically mounted in a range of 15° to 45° from vertical. The purpose of this mounting configuration is to effectively maximize the reflected light off of one half of each DIP switch in housing 115. The intensity of reflected light is strongest on the one side of a switch. The image sent to the image processor must effectively record this information to identify the DIP switch housing 115 position and orientation.

Image processor 125 comprises a computer processor (central processor) 129 and peripheral devices that include input keyboard 128, memory storage device 126, configuration reader 102 and user interface screen 120. Computer processor 129 should have the capacity to analyze each image in the time space of a few seconds. A typical personal computer with a clock speed of 10 Mhz is a sufficient. Storage device 126 stores a lookup table 127 for switch configurations, memory for storage of camera images, and memory for the operation of the image processor and supporting software. Configuration reader 102 is an optional peripheral that reads information from a bar strip on the circuit card that defines the configuration of the DIP switches.

Figure 3:
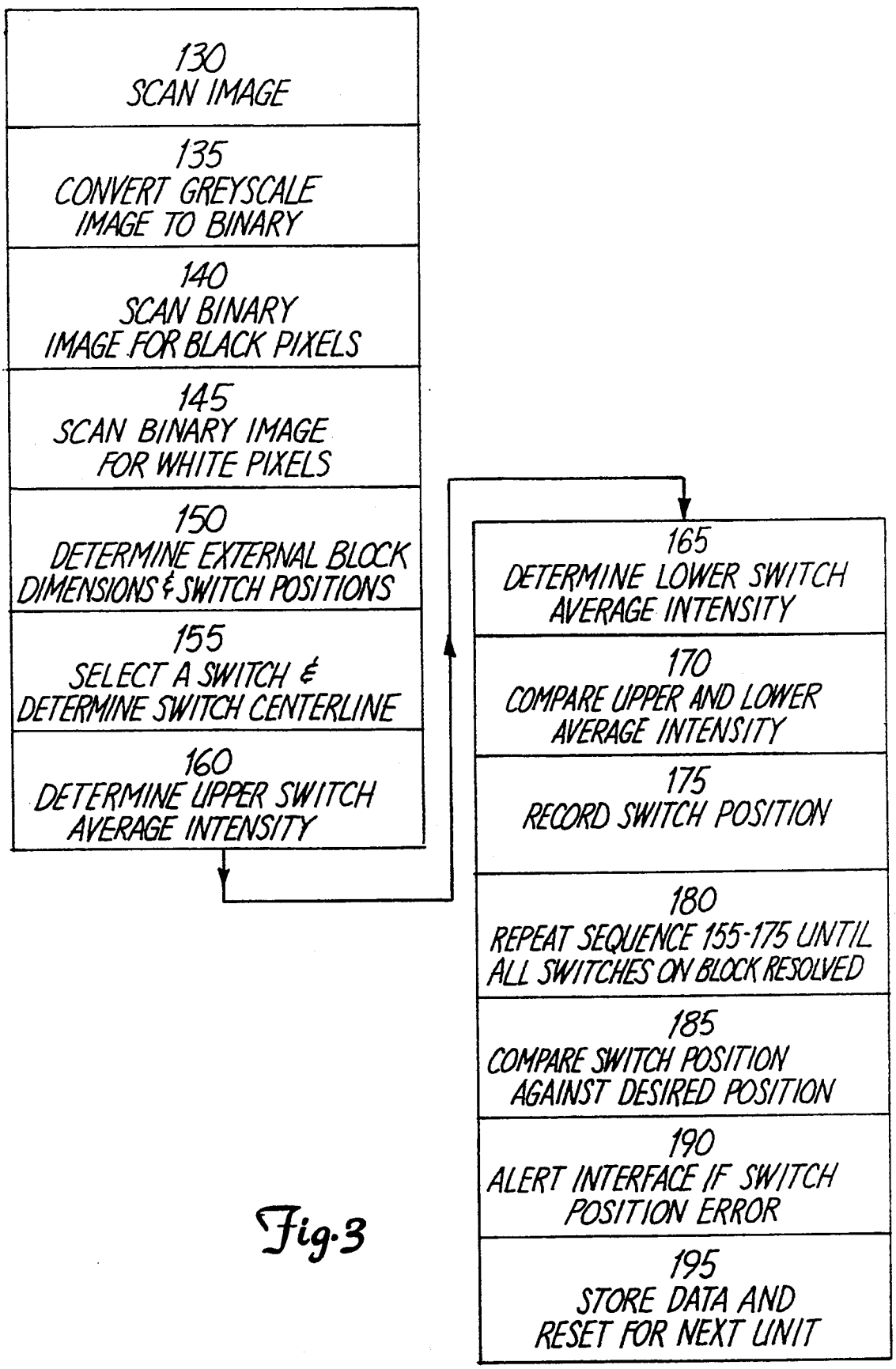
FIG. 3 is a process flow chart of the present invention.

FIG. 3 shows a block diagram of program steps performed by computer 125 in accordance with the invention. At clock 130, the image is scanned and converted to a black and white bit map at block 135 by converting the digital image through a threshold filter that converts all pixel information under an effective threshold range to black and all data over the effective threshold range to white. In one embodiment, black is a grey scale value of 0–25, while white is defined by a grey scale values of 125–255. Ranges used in the preferred embodiment are 0–70 for black area and 80–255 for white area.

A binary image is processed to determine the position of DIP housing 115 on the image. An array then records the DIP image area and an effective area surrounding housing 115. Housing 115 is detected by scanning pixel rows until a continuous line of black pixels is found at program block 140. The continuous row of black pixels represents the top of switch housing 115. Scanning of DIP switch housing 115 continues until the image processor finds a continuous zone of white pixels at block 145 that will represent the bottom edge of the switch that is being processed. Once the top and bottom edges of DIP switch housing 115 are located, this area of the image is analyzed to find right edge 205 and left edge 200 of switch housing 115. The center point of housing 115 is determined after taking the offset error that is introduced by mounting camera 105 at an angle. (E.g. the camera angle will allow some of the corner and side of housing 115 to be recorded as part of the top surface of the DIP switch housing 115.) If housing 115 is rotated more than 30° from normal, this scan may be repeated across an iterative search scan, rotating the image in software until the search requirements are met. If the circuit card is rotated less than 30° from normal, housing 115 is immediately analyzed.

Once the center of DIP switch housing 115 is determined, the right edge 205 and left edge 200 of housing 115 are determined. Edges 200 and 205 are detected by starting at the center point of the top and bottom edges and following the row left or right counting strings of black and white pixels. Edges of individual switches are detected by a change from white to black and then black to white pixels strings. A long string of white pixels indicates the outside edge of housing 115.

At block 155, the centers of each of the individual switches is determined and the vertical centerline column of pixels for each DIP switch is examined at 160 from the horizontal centerline of housing 115 up to the top edge of housing 115. Intensity values of the pixels are averaged over the total number of pixels examined in that half column. This average value for the top half of a switch is saved. The vertical center line column is examined at 165 from the horizontal centerline down to the bottom edge of housing 115. Intensities of each pixel is averaged over the total number of pixels examined and recorded. The bottom averaged value is subtracted from the top averaged value at 170. If the top averaged value is higher than the bottom averaged value, the switch position is in the "OFF" position. Conversely, if the bottom averaged value of the switch is greater than the top averaged value, the switch position is in the "OFF" position. The apparent switch position is then recorded at 175. This analysis technique is repeated at 180 for each switch on DIP switch housing 115.

In operation, a user initializes the unit and selects a board configuration from the look-up table 127. Alternatively, a user may update or create a new configuration if authorized to do so. The scanning sequence is initiated and intermediate scan results are displayed to screen 120. Once the scans are finished, a graphic representation of the switch settings is displayed to the user. The user is also shown the measured intensities of the top and bottom halves of each switch and the relative difference between the top and bottom positions 220. If the settings are incorrect, the user is asked to reset the switches to the correct settings and then to notify the device of the corrected settings at block 190. Circuit board 110 can now be requeued for a confirmation scan or moved forward to another work station. Alternatively, the user interface can be connected to an automated correction device or rework station that automatically resets the switch positions. After the device scan is completed, the information regarding the piece is stored at block 195. After the data processing is complete, the user has the option to exit the scan system, scan another circuit board 110, or conduct configuration updates.

By recording only a differential value, the present invention eliminates the dependency that absolute image recognition systems have on consistent lighting. Analyzing the vertical centerline of a switch allows error in orientation of switch housing 115 to be tolerated as pixel intensity still results in accurate recording even if a portion of the total number of pixels are truncated. In low light intensity conditions, the differential will only be less. The image processor only has to compare the difference in average intensity across the top and bottom to determine switch position. The image processing method also reduces the required processing power of the image processor. By conversion of the grey scale image to binary data and reducing the focus of the processing to a smaller field of view, the system effectively maximizes the desired data and the analysis of image becomes elegantly simple and fast. The usage of relative differences in reflected light intensities eliminates the need for edge detection processing and extensive processing of image data that is ultimately not used. The analysis of pixel rows in an array allows an N×M dimensioned DIP switch housing 115 with X number of individual switches, N the height and M the width, to be analyzed after examining only X×N pixels per DIP switch housing 115.

Other configurations of the present system include the ability to differentiate variably shaped DIP switches or other components and the ability to learn the different DIP switch housing 115 configurations as they are encountered.

Although the present invention has been described with reference to preferred embodiments, workers skilled in the art will recognize that changes may be made in form and detail without departing from the spirit and scope of the invention.

What is claimed is:

1. An automated visual inspection system for determining position of a switch in a DIP switch assembly, comprising:
    an optical sensor for sensing a relative reflected light intensity of a substantially horizontal circuit board, the switch movable between a first position and a second position, and providing a binary image output;
    means for analyzing the binary image and comparing relative intensity of a first portion of the switch with a second portion of the switch and determining position of the switch between the first and second positions; and
    output means providing a first output if the means for analyzing determines the switch is in the first position and a second output if the means for analyzing determines the switch is in the second position.

2. The system of claim 1, including:
    means for storing a desired switch position; and
    means for comparing the desired switch position with the determined switch position and providing an output based upon the comparison.

3. The system of claim 1 wherein the optical sensor is mounted between 15 and 45 degrees offset from a vertical reference.

4. The system of claim 1 including means for converting a grey scale image using a threshold range that increases a reflected light differential between the first and second switch positions.

5. The system of claim 4 wherein the threshold range defines a black pixel in a grey scale value of 0–25 and a white pixel in a grey scale value of 125–255.

6. The apparatus of claim 4 wherein the threshold range defines a black pixel in a grey scale value of 0–70 and a white pixel in a grey scale value of 80–255.

7. The system of claim 1 wherein the means for analyzing includes means for determining average intensity of the first and second portions of the switch and comparing average intensities to determine switch position.

8. A method for determining the relative position of a switch position of a switch located on a horizontally oriented Dual Inline Package switch housing, comprising:
    sensing a reflected light intensity from two relative position surfaces of the switch;
    analyzing the reflected light intensities of the relative position surfaces to resolve an apparent position orientation of the switch;
    comparing an apparent position of the switch to a desired position of the switch; and
    providing an output based upon the step of comparing.

9. The method in claim 8 wherein the step of sensing comprises resolving the reflected intensities into a digitized image.

10. The method in claim 8 including converting reflected intensities into a map of the switch housing using a threshold range that increases a differential of reflected intensities between the relative position surfaces.

11. The method in claim 9 wherein the threshold range defines a black pixel in a grey scale value of 0–25 and a white pixel in a grey scale value of 125–255.

12. The method in claim 9 wherein the threshold range defines a black pixel in a grey scale value of 0–70 and a white pixel in a grey scale value of 80–255.

13. The method in claim 8 wherein the step of analyzing comprises;
    scanning an identified area of the switch housing for a row of black pixels representing a top edge;
    scanning the identified area of the switch housing for a row of white pixels representing a bottom edge;
    locating a centerline between the top edge and the bottom edge;
    scanning along the centerline for a periodic grouping of alternating pixel values to locate edges and a horizontal location of a vertical centerline of a switch;
    recording intensity values of the vertical centerline of pixels above a horizontal centerline; and
    recording intensity values of the vertical centerline of pixels below the horizontal centerline.

14. The method in claim 8 wherein the step of analyzing comprises:
    averaging intensities of vertical centerline pixels with a total number of vertical center line pixels in an upper half of a switch;
    averaging intensities of vertical centerline pixels with a total number of vertical center line pixels in a lower half of the switch; and
    determining an apparent position of the switch by a difference in upper and lower light intensity averages.

* * * * *